United States Patent
Chun

(10) Patent No.: US 11,159,868 B2
(45) Date of Patent: Oct. 26, 2021

(54) ELECTRONIC DEVICE FOR AUTHENTICATING USER BY USING AUDIO SIGNAL AND METHOD THEREOF

(71) Applicant: Samsung Electronics Co., Ltd., Gyeonggi-do (KR)

(72) Inventor: Young Soo Chun, Gyeonggi-do (KR)

(73) Assignee: Samsung Electronics Co., Ltd

( * ) Notice: Subject to any disclaimer, the term of this patent is extended or adjusted under 35 U.S.C. 154(b) by 0 days.

(21) Appl. No.: 16/253,500

(22) Filed: Jan. 22, 2019

(65) Prior Publication Data
US 2019/0230426 A1    Jul. 25, 2019

(30) Foreign Application Priority Data
Jan. 22, 2018 (KR) .................. 10-2018-0007880

(51) Int. Cl.
*H04R 1/10* (2006.01)
*G06F 21/31* (2013.01)
(Continued)

(52) U.S. Cl.
CPC .............. *H04R 1/10* (2013.01); *G06F 21/31* (2013.01); *H04R 1/1091* (2013.01); *H04R 3/00* (2013.01);
(Continued)

(58) Field of Classification Search
CPC ..... H04L 63/0861; G06F 3/165; G06F 21/31; G06F 3/0488; H04R 1/10; H04R 3/00;
(Continued)

(56) References Cited

U.S. PATENT DOCUMENTS 6,067,623 A * 5/2000 Blakley, III ........ G06F 21/6236
707/999.009
6,697,299 B2 * 2/2004 Kato ..................... G06K 9/00
367/136
(Continued)

FOREIGN PATENT DOCUMENTS

CN      105978907 A  *  9/2016
JP      2008-033144       2/2008
(Continued)

OTHER PUBLICATIONS

European Search Report dated Sep. 8, 2020 issued in counterpart application No. 19740916.2-1218, 11 pages.
(Continued)

*Primary Examiner* — Matthew A Eason
*Assistant Examiner* — Kuassi A Ganmavo
(74) *Attorney, Agent, or Firm* — The Farrell Law Firm, P.C.

(57) ABSTRACT

An electronic device is provided. The electronic device includes an interface, and a processor configured to receive an input of a user, output an audio signal by using a first external device connected to the electronic device through the interface, in response to the input of the user, obtain an audio signal reflected on a part of the user of the outputted audio signal, by using the first external device, authenticate the user by using the reflected audio signal and execute a specified function in a unlocked state of the electronic device when the user is a user authenticated for the electronic device.

18 Claims, 13 Drawing Sheets

(51) Int. Cl.
*H04R 3/00* (2006.01)
*H04R 29/00* (2006.01)
*G06F 3/0488* (2013.01)
*H04M 1/247* (2021.01)
*H04M 1/78* (2006.01)
*A61F 11/08* (2006.01)

(52) U.S. Cl.
CPC .............. *H04R 29/00* (2013.01); *A61F 11/08* (2013.01); *G06F 3/0488* (2013.01); *H04M 1/247* (2013.01); *H04M 1/78* (2013.01); *H04R 2400/01* (2013.01)

(58) Field of Classification Search
CPC .. H04R 29/00; H04R 1/1091; G07C 9/00158; A61F 11/08; G06K 9/008; H04M 1/247; H04M 1/78
See application file for complete search history.

(56) References Cited

U.S. PATENT DOCUMENTS

| | | | |
|---|---|---|---|
| 8,187,202 B2 | 5/2012 | Akkermans et al. | |
| 8,705,784 B2 | 4/2014 | Haartsen et al. | |
| 9,118,488 B2 | 8/2015 | Donaldson | |
| 9,189,901 B2 | 11/2015 | Agrafioti et al. | |
| 9,349,235 B2 | 5/2016 | Agrafioti et al. | |
| 10,097,914 B2 | 10/2018 | Petrank | |
| 10,334,350 B2 | 6/2019 | Petrank | |
| 2002/0057805 A1 | 5/2002 | Kato et al. | |
| 2004/0141416 A1 | 7/2004 | Kato et al. | |
| 2004/0215968 A1* | 10/2004 | Rodwell | G06F 21/32 713/186 |
| 2008/0262382 A1 | 10/2008 | Akkermans et al. | |
| 2009/0193519 A1* | 7/2009 | Tamkhane | G06F 21/78 726/19 |
| 2010/0189268 A1 | 7/2010 | Haartsen et al. | |
| 2011/0126280 A1* | 5/2011 | Asano | G06F 21/32 726/19 |
| 2011/0179284 A1* | 7/2011 | Suzuki | G06F 21/32 713/186 |
| 2011/0314530 A1 | 12/2011 | Donaldson | |
| 2012/0015629 A1* | 1/2012 | Olsen | H04W 12/08 455/411 |
| 2012/0202563 A1* | 8/2012 | Rao | G06F 3/023 455/556.1 |
| 2012/0317609 A1* | 12/2012 | Carrara | G06F 21/6218 726/1 |
| 2013/0133042 A1* | 5/2013 | Mercredi | G07C 9/37 726/4 |
| 2013/0244634 A1* | 9/2013 | Garrett | H04M 1/72463 455/418 |
| 2014/0092007 A1* | 4/2014 | Kim | H04N 5/4403 345/156 |
| 2014/0196115 A1* | 7/2014 | Pelykh | G06F 21/554 726/4 |
| 2014/0323089 A1* | 10/2014 | Tang | H04W 12/06 455/411 |
| 2015/0028996 A1 | 1/2015 | Agrafioti et al. | |
| 2015/0116068 A1* | 4/2015 | Kwon | H01F 5/02 336/192 |
| 2016/0072819 A1* | 3/2016 | Chen | H04L 63/0861 726/4 |
| 2017/0372055 A1* | 12/2017 | Robinson | H04W 12/06 |
| 2018/0302391 A1* | 10/2018 | Jones | H04L 63/083 |
| 2018/0307818 A1 | 10/2018 | Yano et al. | |
| 2019/0095653 A1* | 3/2019 | Kurosawa | G06F 3/162 |
| 2019/0213313 A1* | 7/2019 | Koshinaka | A61B 5/117 |

FOREIGN PATENT DOCUMENTS

| | | | |
|---|---|---|---|
| JP | 2008077190 A | * | 4/2008 |
| KR | 1020110107831 | | 10/2011 |
| WO | WO-2014088202 A1 | * | 6/2014 |
| WO | WO 2017/069118 | | 4/2017 |
| WO | WO 2017/203484 | | 11/2017 |

OTHER PUBLICATIONS

International Search Report dated May 13, 2019 issued in counterpart application No. PCT/KR2019/000835, 3 pages.

* cited by examiner

ELECTRONIC DEVICE FOR AUTHENTICATING USER BY USING AUDIO SIGNAL AND METHOD THEREOF

CROSS-REFERENCE TO RELATED APPLICATION(S)

This application is based on and claims priority under 35 U.S.C. § 119 to Korean Patent Application Ser. No. 10-2018-0007880, filed on Jan. 22, 2018, in the Korean Intellectual Property Office, the entire disclosure of which is incorporated herein by reference.

BACKGROUND

1. Field

The present disclosure relates generally to an electronic device and a method of authenticating a user by using an audio output device connected to an electronic device.

2. Description of Related Art

An electronic device may be locked for security. The electronic device may perform user authentication to be unlocked. The electronic device may confirm that the user who operates the electronic device is a user having authority.

In addition, various services executed by an electronic device may require user authentication for security. For example, a payment function, a remittance function, and the like, which are performed by a payment service, a banking service, and the like, may be performed only after the user authentication is completed. Before performing the functions, the electronic device may confirm whether the user who intends to perform the functions has a right to perform the functions.

When a user wishes to use an electronic device, the user must perform user authentication for the electronic device. When the authentication is completed, the locked electronic device is unlocked, and the user can use the electronic device.

For authentication, a user may separately perform an operation of inputting authentication information such as a fingerprint input, a password input, an utterance input for a security phrase, and the like. Therefore, since the user must first perform another operation in order to use an intended function of the electronic device, it may be difficult to seamlessly use the electronic device.

In addition, various functions (e.g., programs, files, etc.) executed by an electronic device may require additional authentication procedures for security. For example, to use the above various functions, a user must perform authentication for the electronic device and authentication for the functions, respectively.

Accordingly, it may be difficult to provide intuitive and fast service through an electronic device, and the service provided to a user who has not performed the authentication may be limited. In addition, the user may be inconvenienced due to an errors that occur when a user performs authentication.

SUMMARY

Accordingly, an aspect of the present disclosure is to provide an electronic device for enabling a user to use the electronic device and functions executed by the electronic device without performing a separate operation for user authentication.

In accordance with an aspect of the present disclosure, an electronic device is provided. The electronic device includes an interface, and a processor configured to receive an input of a user, output an audio signal by using a first external device connected to the electronic device through the interface, in response to the input of the user, obtain an audio signal reflected on a part of the user of the outputted audio signal, by using the first external device, authenticate the user by using the reflected audio signal and execute a specified function in a unlocked state of the electronic device when the user is a user authenticated for the electronic device.

In accordance with an aspect of the present disclosure, an electronic device is provided. The electronic device includes an interface that connects an audio output device and the electronic device, an audio circuit that transmits an audio signal to the audio output device connected to the electronic device through the interface, a memory that includes user authentication information about a registered user of the electronic device and instructions, and at least one processor that is electrically connected to the memory. When executed, the instructions cause the at least one processor to transmit a test signal to the audio output device through the audio circuit, receive a feedback signal corresponding to the test signal from the audio output device through the audio circuit, and unlock the electronic device in a lock state when a user wearing the audio output device is indicated as the registered user based on the received feedback signal and the user authentication information.

In accordance with an aspect of the present disclosure, a method performed by an electronic device is provided. The method includes transmitting a test signal to an audio output device connected to the electronic device through a wired interface for a previously specified time, and receiving a feedback signal corresponding to the test signal from the audio output device, and when a user wearing the audio output device is indicated as a registered user of the electronic device, based on the received feedback signal and user authentication information, unlocking the electronic device in a lock state.

BRIEF DESCRIPTION OF THE DRAWINGS

The above and other aspects, features and advantages of certain embodiments of the disclosure will be more apparent from the following detailed description taken in conjunction with the accompanying drawings, in which.

DETAILED DESCRIPTION

Figure 1A:
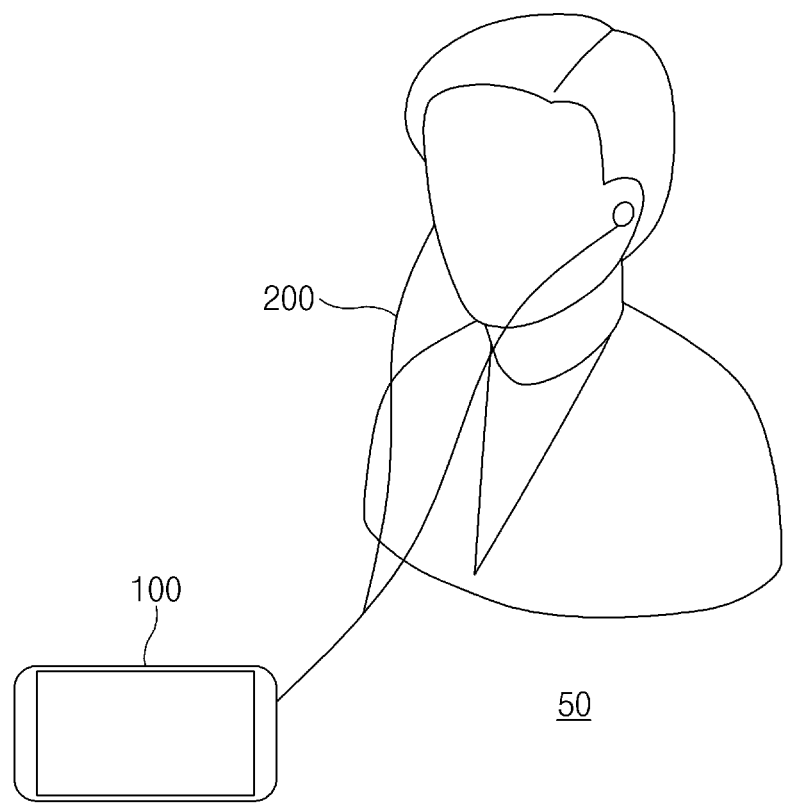
FIG. 1A is a diagram of an operating environment of an electronic device, according to an embodiment.

Hereinafter, various embodiments of the present disclosure may be described with reference to accompanying drawings. Accordingly, those of ordinary skill in the art will recognize that modification, equivalent, and/or alternative on the various embodiments described herein can be variously made without departing from the scope and spirit of the present disclosure. With regard to description of drawings, similar components may be marked by similar reference numerals.

In the present disclosure, the expressions "have", "may have", "include" and "comprise", or "may include" and "may comprise" used herein indicate existence of corresponding features (e.g., components such as numeric values, functions, operations, or parts) but do not exclude presence of additional features.

In the present disclosure, the expressions "A or B", "at least one of A or/and B", or "one or more of A or/and B", and the like may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used in the present disclosure may be used to refer to various components regardless of the order and/or the priority and to distinguish the relevant components from other components, but do not limit the components. For example, "a first user device" and "a second user device" indicate different user devices regardless of the order or priority. For example, without departing the scope of the present disclosure, a first component may be referred to as a second component, and similarly, a second component may be referred to as a first component.

It will be understood that when a component (e.g., a first component) is referred to as being "(operatively or communicatively) coupled with/to" or "connected to" another component (e.g., a second component), it may be directly coupled with/to or connected to the other component or an intervening component (e.g., a third component) may be present. In contrast, when a component (e.g., a first component) is referred to as being "directly coupled with/to" or "directly connected to" another component (e.g., a second component), it should be understood that there are no intervening component (e.g., a third component).

According to the situation, the expression "configured to" used in the present disclosure may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other parts. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

Terms used in the present disclosure are used to describe specified embodiments and are not intended to limit the scope of the present disclosure. The terms of a singular form may include plural forms unless otherwise specified. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal unless expressly so defined in various embodiments of the present disclosure. In some cases, even if terms are defined in the present disclosure, they may not be interpreted to exclude embodiments of the present disclosure.

An electronic device according to various embodiments of the present disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to various embodiments, the wearable device may include at least one of an accessory type (e.g., watches, rings, bracelets, anklets, necklaces, glasses, contact lens, or head-mounted-devices (HMDs)), a fabric or garment-integrated type (e.g., an electronic apparel), a body-attached type (e.g., a skin pad or tattoos), or a bio-implantable type (e.g., an implantable circuit).

According to various embodiments, the electronic device may be a home appliance. The home appliances may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ or PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, automated teller machines (ATMs), points of sales (POSs) devices of stores, or Internet of things (IoT) devices (e.g., light bulbs, various sensors, electric or gas meters, sprinkler devices, fire alarms, thermostats, street lamps, toasters, exercise equipment, hot water tanks, heaters, boilers, and the like).

According to an embodiment, the electronic device may include at least one of parts of furniture or buildings/structures, electronic boards, electronic signature receiving devices, projectors, or various measuring instruments (e.g., water meters, electricity meters, gas meters, or wave meters, and the like). According to various embodiments, the electronic device may be one of the above-described devices or a combination thereof. An electronic device according to an embodiment may be a flexible electronic device. Furthermore, an electronic device according to an embodiment of the present disclosure may not be limited to the above-described electronic devices and may include other electronic devices and new electronic devices according to the development of technologies.

Hereinafter, electronic devices according to various embodiments will be described with reference to the accompanying drawings. In the present disclosure, the term "user" may refer to a person who uses an electronic device or may refer to a device (e.g., an artificial intelligence electronic device) that uses the electronic device.

Figure 1B:
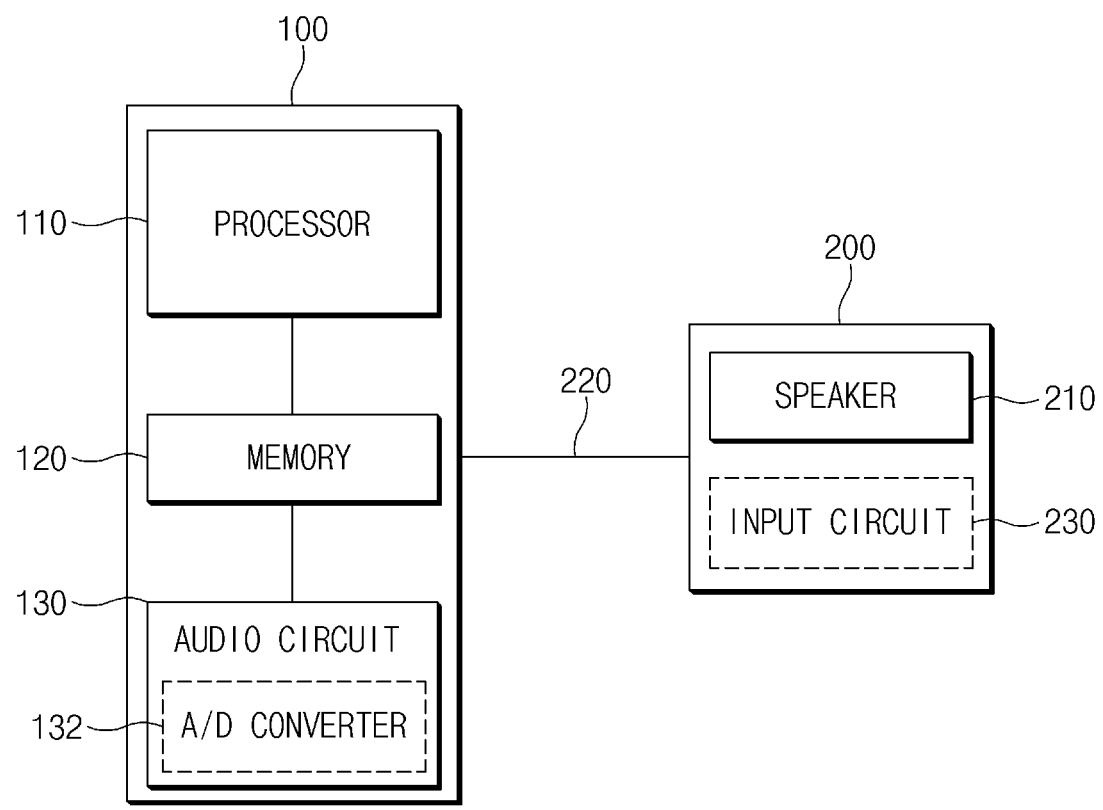
FIG. 1B is a diagram of an electronic device and an audio output device, according to an embodiment.
Figure 1C:
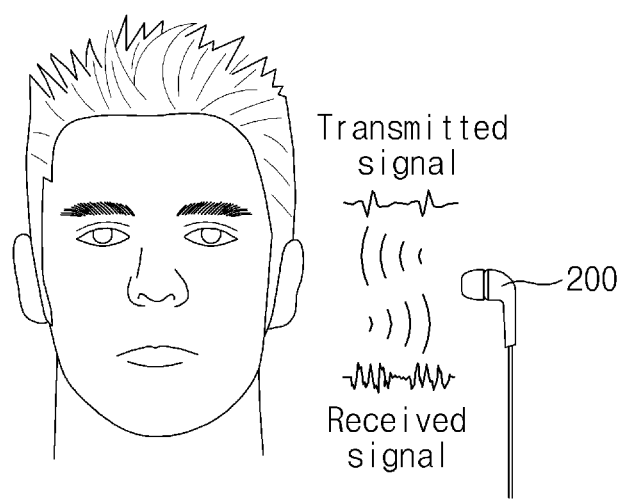
FIG. 1C is a diagram of a speaker included in an audio output device, according to an embodiment.
Figure 1C:
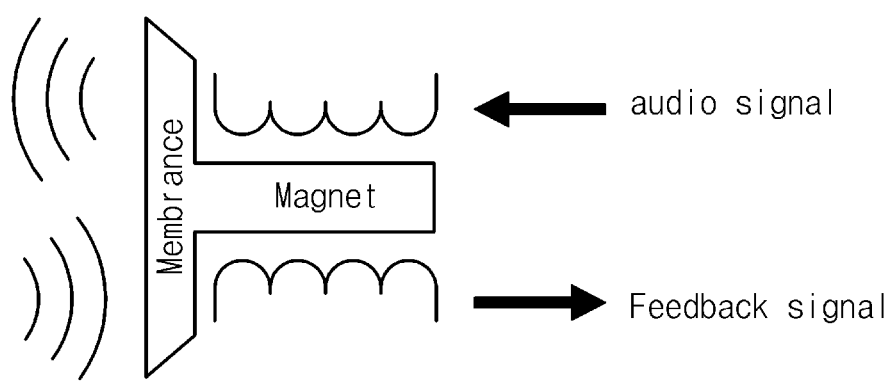
Figure 1D:
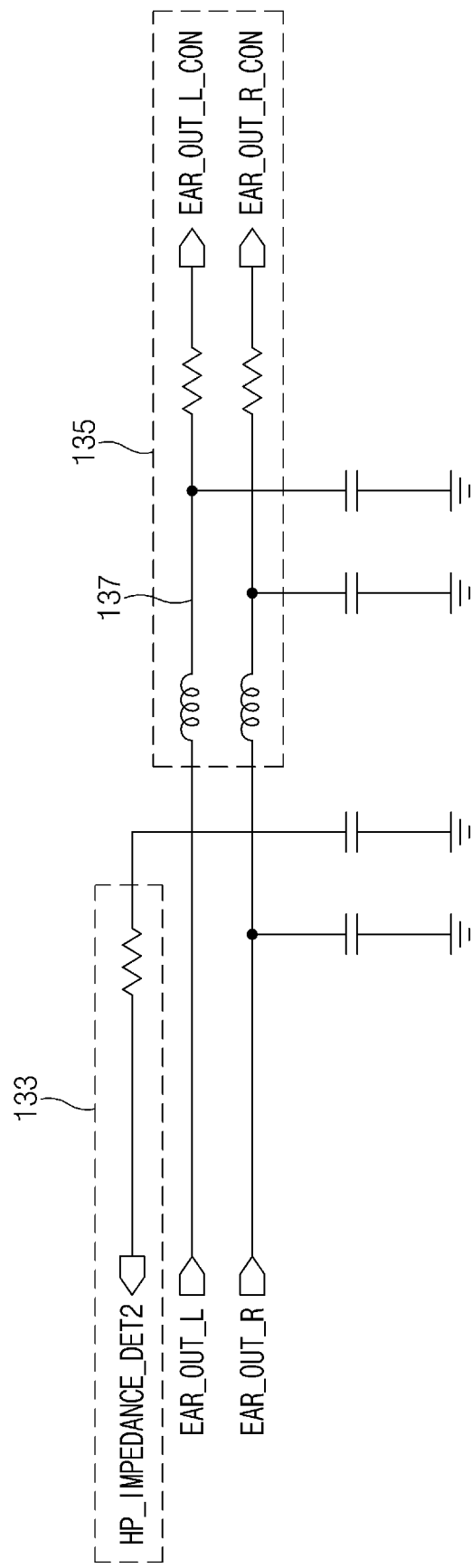
FIG. 1D is a diagram of a partial circuit diagram included in an audio circuit, according to an embodiment.

FIG. 1A is a diagram of an operating environment of an electronic device, according to an embodiment. FIG. 1B is a diagram of an electronic device and an audio output device, according to an embodiment. FIG. 1C is a diagram of a schematic structure of a speaker included in an audio output device, according to an embodiment. FIG. 1D is a partial circuit diagram included in an audio circuit, according to an embodiment.

Referring to FIG. 1A, an electronic device 100 may be referred to as a terminal of a user 50 such as a smartphone, a tablet PC, and the like. An audio output device 200 may be referred to as an audio device worn by the user 50 such as an earphone, and the like. The user 50 may wear the audio output device 200 (e.g., an earphone). The user 50 may use the electronic device 100 (e.g., a smart phone, a tablet PC, etc.) while wearing the audio output device 200. The electronic device 100 may use the audio output device 200 to determine whether the user 50 is authorized to use the electronic device 100. The user 50 may perform the user authentication by wearing the audio output device 200 and use the electronic device 100.

Referring to FIG. 1B, the electronic device 100 may include a processor 110, a memory 120, and an audio circuit 130.

The processor 110 may be electrically coupled to the memory 120 and the audio circuit 130. The processor 110 may directly or indirectly control the memory 120 and the audio circuit 130. The processor 110 may be referred to as an application processor (AP). Hereinafter, the operation of the electronic device 100 described may be performed by the processor 110.

The audio circuit 130 may be set to transmit and receive audio signals between the electronic device 100 and the audio output device 200 connected to the electronic device 100. The audio output device 200 may be connected to the electronic device 100 through a wired or wireless interface 220. The wired interface 220 may be referred to as a wired cable. The wireless interface 220 may be referred to as a wireless communication channel (e.g., Bluetooth) formed between the audio output device 200 and the electronic device 100. The audio circuit 130 may transmit or receive an audio signal to or from the audio output device 200 through the interface 220.

The audio output device 200 may include a speaker 210. The audio output device 200 may output the received audio signal through the speaker 210.

The memory 120 may include user authentication information about a registered user of the electronic device 100. The registered user may be referred to as a user registered in advance to have the authority to use the electronic device 100. The user authentication information may be referred to as data used to determine whether the user who operates the electronic device 100 is a registered user.

The memory 120 may include instructions. The processor 110 may execute the instructions stored in the memory 120 and may control the overall operation of the electronic device 100.

The electronic device 100 may transmit an audio signal to the audio output device 200 through the audio circuit 130. The electronic device 100 may receive a feedback signal corresponding to the audio signal from the audio output device 200 through the audio circuit 130. The audio signal may be reflected in the ear of a user wearing the audio output device 200 and input as a feedback signal. The feedback signal may have different properties (e.g., waveforms) by people.

Referring to FIG. 1C, when the speaker 210 receives an audio signal from the electronic device 100, the audio signal may be transmitted to the ear of the user 50. The audio signal may be reflected in the ear of the user 50 and received by the electronic device 100 through the speaker 210 again. The audio signal may be transmitted to the eardrum and reflected after passing through the ear canal of the user 50. The reflected and received audio signal may be referred to as a feedback signal. Hereinafter, among the audio signals transmitted to the audio output device 200, the audio signal transmitted to obtain the feedback signal may be described as a test signal.

When it is indicated that the user wearing the audio output device 200 is a registered user, based on the received feedback signal and the user authentication information stored in the memory 120, the electronic device 100 may unlock the electronic device 100 of a lock state. The electronic device 100 may confirm that the user wearing the audio output device 200 is a user authorized to operate the electronic device 100 (user authentication) and may unlock the electronic device 100.

The user authentication information stored in the memory 120 may include data on a feedback signal corresponding to a registered user. When there are multiple registered users, the user authentication information may include authentication data related to feedback signals corresponding to each of the users. The electronic device 100 may perform user authentication with reference to the feedback signal and the authentication information of the user.

The audio circuit 130 may further include an analog to digital (A/D) converter 132. The A/D converter 132 may analyze a voltage value of the received feedback signal and extract a digital signal.

The electronic device 100 may obtain pulse code modulation (PCM) data corresponding to the feedback signal through the A/D converter 132. Data on the feedback signal included in the user authentication information may be referred to as the PCM data.

Referring to FIG. 1D, the audio circuit 130 of the electronic device 100 may include a feedback signal input unit 133 and an audio signal output unit 135. The audio signal output unit 135 of the audio circuit 130 may output an audio signal to the audio output device 200. The output audio signal may be reflected by a part of the user 50 and input to the feedback signal input unit 133 through an output line 137 of the audio signal output unit 135. The input feedback signal may be transmitted to the A/D converter 132 and converted to PCM data.

The audio output device 200 may further include an input circuit 230. The audio output device 200 may receive a tap input, a touch input, and the like through the input circuit 230. The user may transmit a control command for the electronic device 100 through the input circuit 230.

Figure 1E:
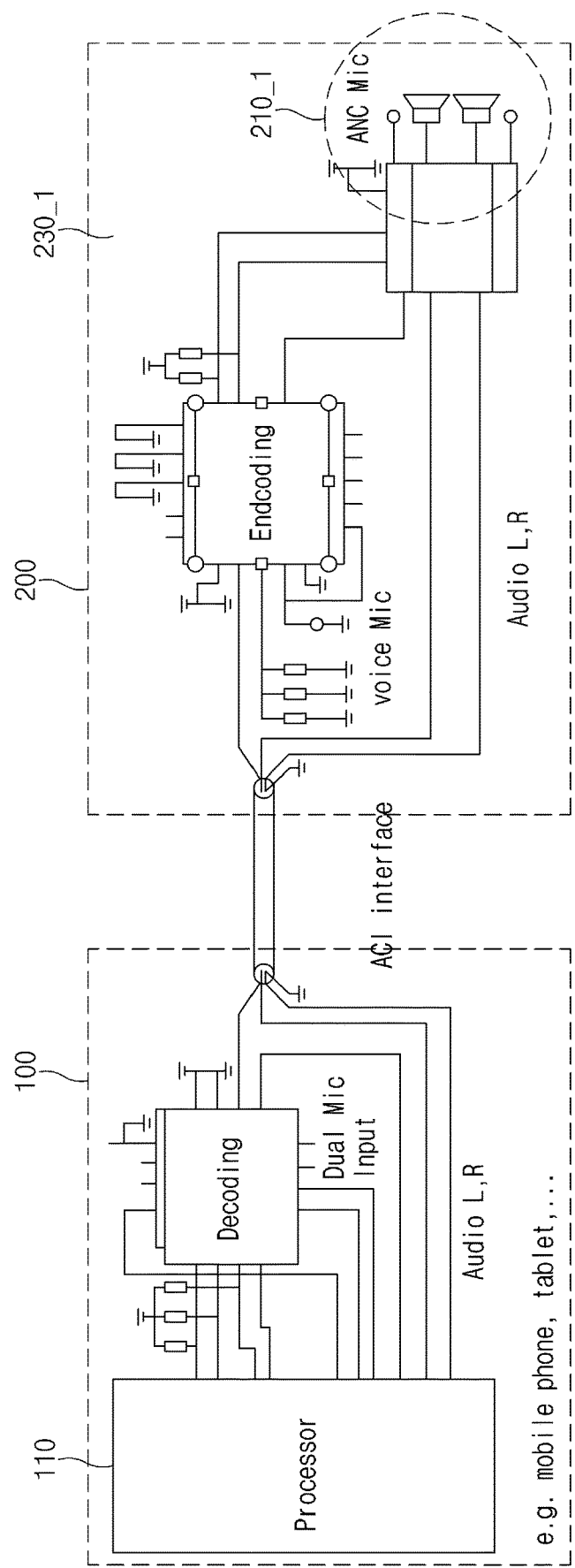
FIG. 1E is a diagram of an audio output device including a microphone and an electronic device, according to an embodiment.

FIG. 1E is a partial circuit diagram of an audio output device including a microphone and an electronic device, according to an embodiment.

Referring to FIG. 1E, the audio output device 200 (e.g., an earphone that supports a noise cancelling function) may further include a microphone. The audio output device 200 may include a speaker 210_1 including a microphone. The audio output device 200 may receive the feedback signal through the microphone. The audio output device 200 may separate the feedback signal obtained from the microphones included in the speaker 210_1 and the voice signal obtained from a voice microphone (voice Mic) of the user in time division multiplexing (TDM), and transmit them to the electronic device 100, through an input circuit 230_1. The electronic device 100 may authenticate the user by using the received feedback signal.

An audio output device (e.g., the audio output device 200 of a digital type) may include a microphone and an A/D converter. In this case, the audio output device may directly analyze the feedback signal obtained from the microphone and perform user authentication. The electronic device 100 may receive the result of authenticating the user from the audio output device and perform a lock/unlock operation on the electronic device based on the authentication result.

Figure 2:
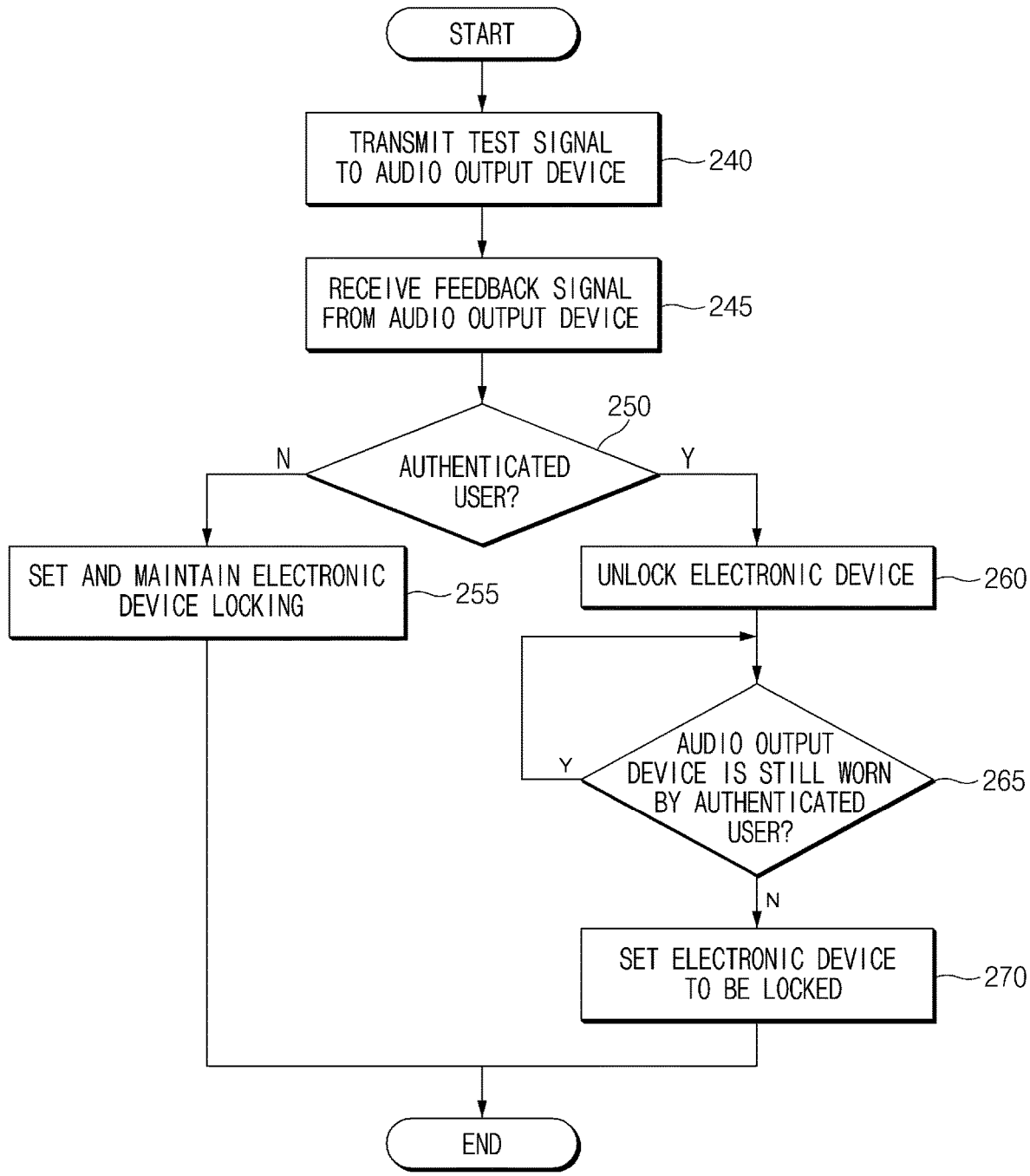
FIG. 2 is a flowchart for a user authentication method, according to an embodiment.

FIG. 2 is a flowchart of a user authentication method, according to an embodiment.

Referring to FIG. 2, a user authentication method may include steps 240 to 270. For example, the steps 240 to 270 may be performed by the electronic device 100 shown in FIG. 1B. Each of the steps 240 to 270 may be implemented with instructions that may be performed (or executed) by, for example, the processor 110 of the electronic device 100. For example, the instructions may be stored in a computer recording medium or in the memory 120 of the electronic device 100 shown in FIG. 1B. In the following description of steps 240 to 270, the description overlapping with the description of FIG. 1B will be omitted.

At step 240, the electronic device may transmit a test signal to the audio output device. At step 245, the electronic device may receive a feedback signal corresponding to the test signal.

The test signal may be transmitted to authenticate a user wearing the audio output device. The test signal may be transmitted to the audio output device for a specified time. The electronic device may receive a feedback signal corresponding to the test signal for the specified time. The electronic device may perform user authentication based on the feedback signal received for the specified time.

The test signal may be transmitted to measure the impedance of the audio output device. In this case, the test signal may be transmitted for a time shorter than the time specified for authentication. The electronic device may determine the impedance of the audio output device through the feedback signal corresponding to the transmitted test signal. For example, the electronic device may use the A/D converter to determine the impedance. The electronic device may determine the level of the audio signal to be transmitted to the audio output device based on the determined impedance.

The electronic device may be referred to as a portable device such as a smart phone. The electronic device may include the A/D converter for compatibility with various types of audio output devices. The electronic device may determine the impedance values of various audio output devices by using the A/D converter of the audio circuit and may output audio signals corresponding thereto. The electronic device may perform user authentication by diverting the A/D converter for impedance measurement without adding a separate configuration to the audio circuit.

At step 250, the electronic device may perform user authentication. At step 260, the electronic device may unlock the electronic device when the user authentication is successful and at step 255, may set or maintain the lock of the electronic device when the user authentication fails.

At step 250, the electronic device may obtain PCM data corresponding to the feedback signal received for the specified time. The PCM data may include consecutive digital signal values obtained by the A/D converter. Since the feedback signal obtained for each user has a unique property, the PCM data corresponding to the feedback signal may have a unique value for each user. The electronic device may perform the user authentication by comparing the PCM data with the user authentication information.

The user authentication information may include authentication data mapped with each user. The authentication data may be referred to as PCM data corresponding to a specific user. For example, the PCM data converted from the feedback signal for each user may have a unique value. The user authentication information is illustrated in following Table 1. The authentication data '0011101011101' for registered user 'A' and the authentication data '1001101111100' for registered user 'B' are illustrated.

TABLE 1

| Registered user | Authentication data (e.g., PCM data) |
| --- | --- |
| A | 0011101011101 |
| B | 1001101111100 |

When the electronic device obtains the PCM data, the electronic device may compare the PCM data with previously stored authentication data. The electronic device may authenticate a user wearing the audio output device as a registered user when the authentication data matching the obtained PCM data exist. The electronic device is unlocked and the user wearing the audio output device may use the electronic device.

At step 265, the electronic device may confirm whether the audio output device is still worn by the authenticated user. At step 270, the electronic device may change the unlocked state of the electronic device to the lock state when the audio output device detects a state where the audio output device is not worn by the authenticated user. The electronic device may perform authentication and de-authentication by detecting the attachment and detachment of the audio output device.

The electronic device may detect a state where the audio output device is not worn by a user or a state where the audio output device is worn by another unauthenticated user.

The electronic device may transmit the test signal to the audio output device every specific period. The constant period may be specified in advance. The electronic device may determine from the feedback signal corresponding to the test signal that the user is not wearing the audio output device or the audio output device is worn by another user.

When the PCM data are meaningless PCM data that do not include a certain pattern generated by a body of the user, the electronic device may determine that the audio output device is not worn by the user. When PCM data having a pattern different from that of the PCM data of the authenticated user are obtained, the electronic device may determine the state as the audio output device is worn by an unauthenticated user.

Figure 3:
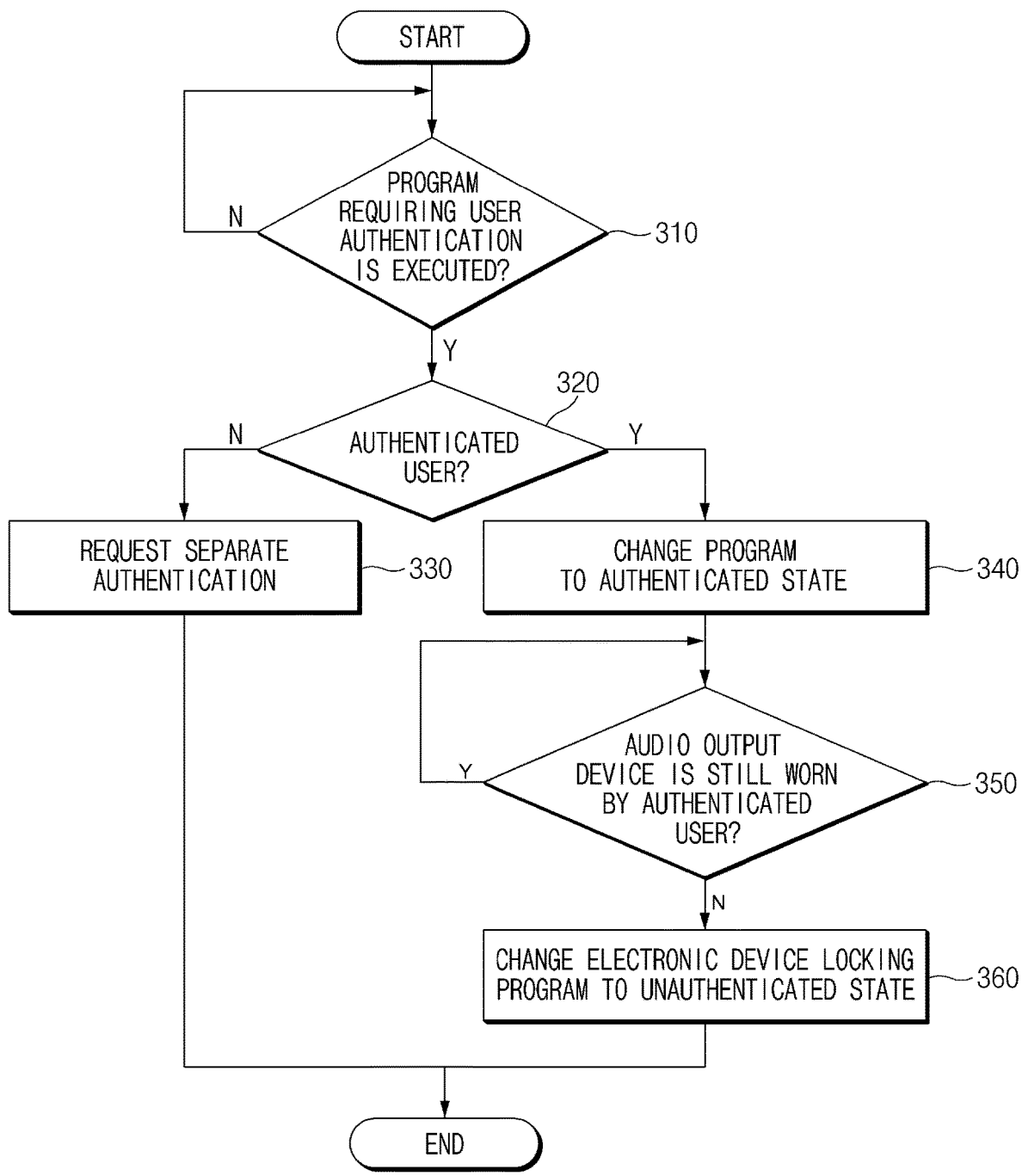
FIG. 3 is a flowchart for a method for authenticating a user for a specific program, according to an embodiment.

FIG. 3 is a flowchart for a method for authenticating a user for a specific program, according to an embodiment.

Referring to FIG. 3, a user authentication method may include steps 310 to 360. The steps 310 to 360 may be performed by the processor 110 of the electronic device 100 shown in FIG. 1B. The step 320 may correspond to the operation 240, 245, and 250 of FIG. 2. The steps 350 to 360 may correspond to the steps 265 to 270 of FIG. 2. In the following description of steps 310 to 360, the description overlapping with the description of FIGS. 1B and 2 will be omitted.

At step 310, the electronic device may detect the execution of a program which requires user authentication. At step 320, the electronic device may perform user authentication for the program based on the feedback signal and user authentication information. At step 340, the electronic device may change an unauthenticated state of the program to an authenticated state when the user authentication is successful. The electronic device may allow a program requiring authentication information to be executed without requesting the user for additional authentication information.

A program that requires user authentication may be referred to as a payment program, a social networking service (SNS) program, an online banking program, or the like. The user is not required to input authentication information when performing payment through the payment program, logging into the SNS program, or transferring money through the online banking program.

When the user authentication fails, at step 330, the electronic device may request separate authentication information for the program. The electronic device may display an image of requesting login information or an image of requesting a password input.

At step 350, the electronic device may confirm whether the audio output device is still worn by the authenticated user. At step 360, when the electronic device detects a state in which the audio output device is not worn by the authenticated user, the electronic device may change an authenticated state of the program to an unauthorized state. The electronic device may perform authentication and de-authentication for a specific program by detecting the detachment of the audio output device.

When a program requiring user authentication is executed by the unlocked electronic device, the electronic device may omit the user authentication procedure for the program. Since the user authentication for the electronic device has already been completed, the authentication procedure for the program may be omitted. When the authentication for the electronic device is completed, the user may execute various programs without performing any additional authentication operations. In this case, when the electronic device detects that the audio output device is not worn by the authenticated user, the electronic device in the unlocked state is locked and the program in the authenticated state may be changed to the unauthenticated state.

Steps 310 to 360 may be performed similarly even when a file with a restricted user access is executed. The electronic device may allow access to the file to the authenticated user. For example, the file may include a media file such as a photo, music, an image, and the like, or a folder created by the user.

The user authentication information may include user authority information of a plurality of programs. The user authentication information may include a list of programs that can be authenticated by the audio output device. For example, referring to Table 2, when the authentication for user 'A' is completed, the user 'A' may execute payment program '1' and voice command program '2' without any additional authentication procedures. When the authentication for user 'B' is completed, the user 'B' may execute the voice command program '2' without any additional authentication, and may access file '3' without any additional authentication. The user may specify the program list in advance for allowing authentication by the audio output device.

TABLE 2

| Registered user | Authentication data | Program authority information |
|---|---|---|
| A | 0011101011101 | Payment program 1 |
|   |   | Voice command program 2 |
| B | 0011101011101 | Voice command program 2 |
|   |   | File 3 |

Figure 4A:
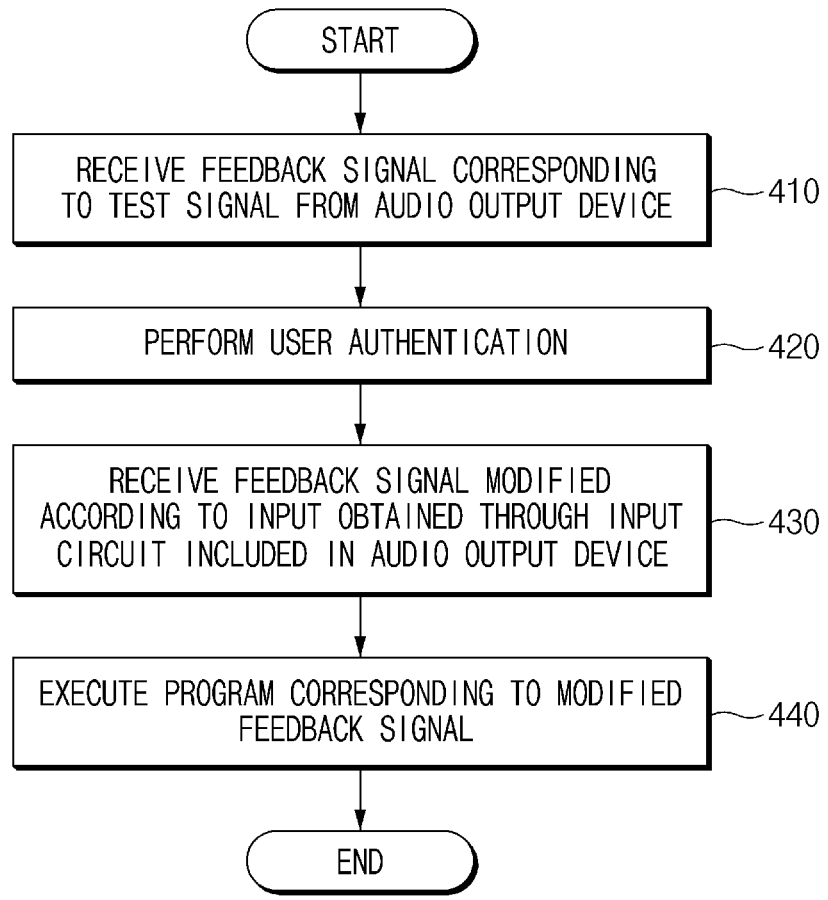
FIG. 4A is a flowchart for a method of performing a function corresponding to an input of a user, according to an embodiment.
Figure 4B:
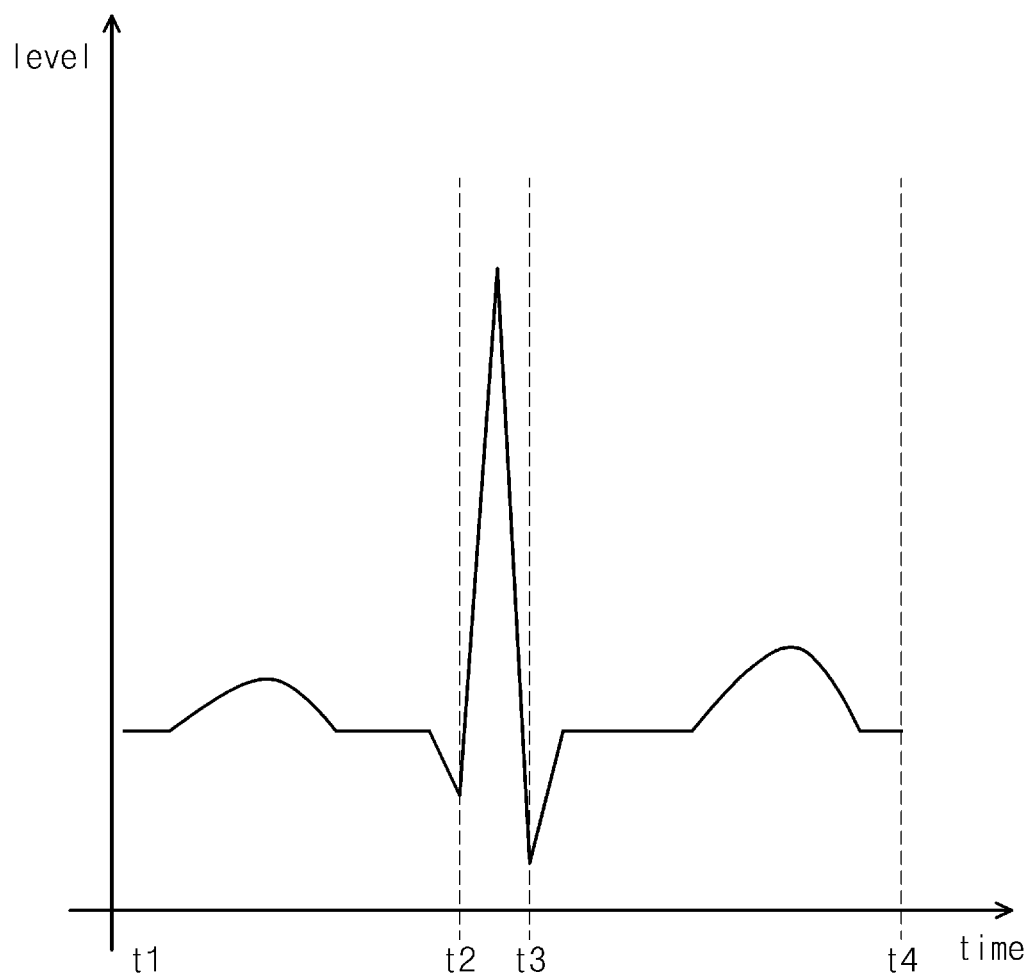
FIG. 4B is a diagram of an example feedback signal, according to an embodiment.

FIG. 4A is a flowchart for a method of performing a function corresponding to an input of a user, according to an embodiment. FIG. 4B is a diagram of an example feedback signal, according to an embodiment.

Referring to FIG. 4A, a method of performing a function may include steps 410 to 440. In the following description of steps 410 to 440, the description overlapping with the description of FIGS. 1B and 2 will be omitted.

At steps 410 and 420, the electronic device may transmit a test signal to the audio output device and may receive a feedback signal corresponding to the test signal from the audio output device. The electronic device may perform user authentication by using the feedback signal.

The electronic device may extract PCM data from the feedback signal by using the A/D converter. First PCM data corresponding to the feedback signal may be compared with second PCM data (e.g., the authentication data shown in Table 1) stored in advance corresponding to a specific user. When the first PCM data and the second PCM data are matched with each other, the electronic device may complete the authentication for the specific user corresponding to the second PCM data. The electronic device may identify the user wearing the audio output device (e.g., an earphone) through the authentication scheme.

The second PCM data corresponding to the specific user may be stored in memory in advance. The electronic device may support a 'training mode' in which the authentication data for the specific user are obtained. In the training mode, the electronic device may obtain the feedback signal for the specific user and store the PCM data extracted from the obtained feedback signal in the memory. Thereafter, the electronic device may perform authentication for the specific user by using the stored PCM data. The electronic device may compare the stored PCM data with the obtained PCM data and may complete the authentication when both data are matched with each other. In following description, it is assumed that the user authentication is successful.

At step 430, the electronic device may receive the feedback signal modified in accordance with the input obtained through the input circuit included in the audio output device.

At step 440, the electronic device may perform at least one function corresponding to the modified feedback signal.

The input circuit of the audio output device may receive an input of a user. The input circuit may include a physical button and may receive a tap input through the physical button. The input circuit may include a touch pad, and may receive a touch input through the touch pad. The electronic device may receive different types of inputs, such as one tap input, a touch input for two seconds, and the like, through the input circuit.

The input circuit may be arranged on the interface through which the feedback signal is received. The feedback signal may be modified in accordance with the input obtained by the input circuit. The feedback signal may be modified in accordance with a touch input or a tap input through the input circuit.

For example, referring to FIG. 4B, an example of a feedback signal when the tap input occurs once is shown. The electronic device may perform the user authentication of step 420 based on the feedback signal from t1 to t2. When the tap input is inputted from t3 to t4 through the input circuit, the feedback signal may be modified. The electronic device may perform a function corresponding to the feedback signal modified from t3 to t4. Alternatively, the electronic device may perform a function corresponding to the feedback signal modified after the input (after t3).

When the electronic device receives the modified feedback signal, the electronic device may extract third PCM data from the modified feedback signal. The electronic device may perform a function mapped to fourth PCM data stored in advance when the fourth PCM data stored in advance matches the third PCM data. The electronic device may store in advance fourth PCM data and the mapping information of the function to be performed corresponding to the fourth PCM data in the memory.

The electronic device may learn feedback signals of various patterns modified by a user. A user may perform a specific input and may specify a function to be performed corresponding to the specific input. The electronic device may receive the feedback signal modified according to the specific input and extract the third PCM data from the modified feedback signal. The electronic device may store the mapping information of the third PCM data and the function to be executed corresponding to the specific input. A plurality of feedback signals of different patterns may be mapped to a plurality of different functions. The processor of the electronic device may be set to perform a specific function corresponding to the modified feedback signal upon receiving the feedback signal modified according to a specific input after the user authentication is performed.

Figure 5:
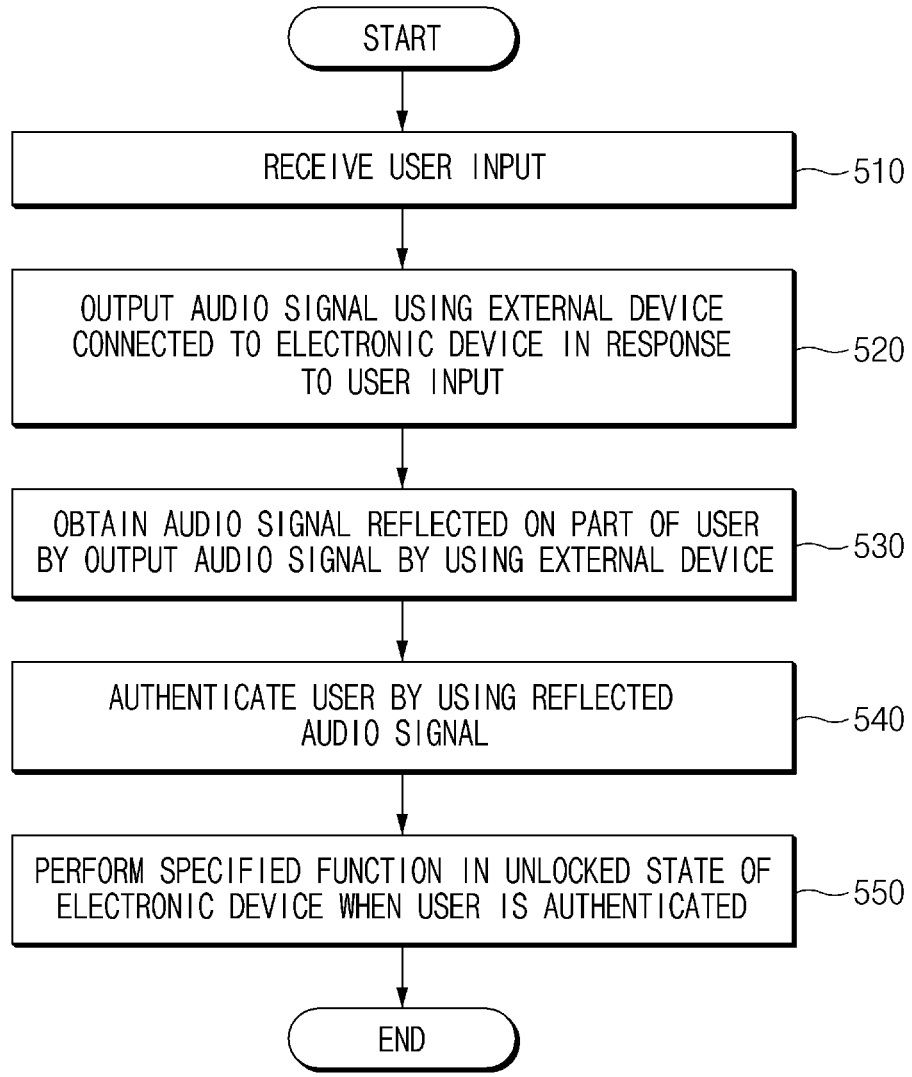
FIG. 5 is a flowchart for a user authentication method, according to an embodiment.

FIG. 5 is a flowchart of a user authentication method, according to an embodiment.

Referring to FIG. 5, a user authentication method may include steps 510 to 550. In the following description, the description overlapping with the description of FIGS. 1B and 2 will be omitted.

At step 510, the electronic device may receive a user input. The user input may be a command to execute a function which requires user authentication. The user may input utterance to the electronic device to invoke a speech recognition service. The electronic device may perform the user authentication before executing the speech recognition service corresponding to the utterance input.

At step 520, the electronic device may output an audio signal by using an external device connected to the electronic device in response to the user input. The external device may be referred to as an earphone (e.g., the audio output device 200 of FIG. 1B). The electronic device may output an audio signal through the external device to perform authentication for a user wearing the external device.

At step 530, the electronic device may use the external device to obtain an audio signal that is reflected on a part of the user by the output audio signal. The audio signal output through the earphone may be reflected on the ear canal of the user.

At step 540, the electronic device may perform the user authentication by using the reflected audio signal. The audio signal reflected on the user may have a pattern unique for each user. The electronic device may perform the user authentication by comparing the obtained audio signal with a previously stored pattern.

The electronic device may extract PCM data from the reflected audio signal by using the A/D converter. The processor of the electronic device may compare the extracted PCM data with the previously stored PCM data (e.g., the authentication data in Table 1). When both data are matched with each other, the authentication of the user corresponding to the previously stored PCM data may be completed.

At step 550, the electronic device may perform the specified function in an unlocked state of the electronic device when the user authentication is complete. The specified function may be referred to, for example, as a function corresponding to the user input received in the step 510. The electronic device may execute a voice input service.

At step 550, the electronic device may obtain a voice input for performing a specific function from a user. The electronic device may transmit the voice input or text data corresponding to the voice input to an external device (e.g., a server). The electronic device may include an automatic speech recognition (ASR) module. The electronic device may convert the voice input into text data by using the ASR module. The external device may generate an instruction related to the specific function by using the voice input or text data received. The external device may transmit the generated instruction to the electronic device 100. The electronic device may execute the specific function based on the instruction.

Figure 6:
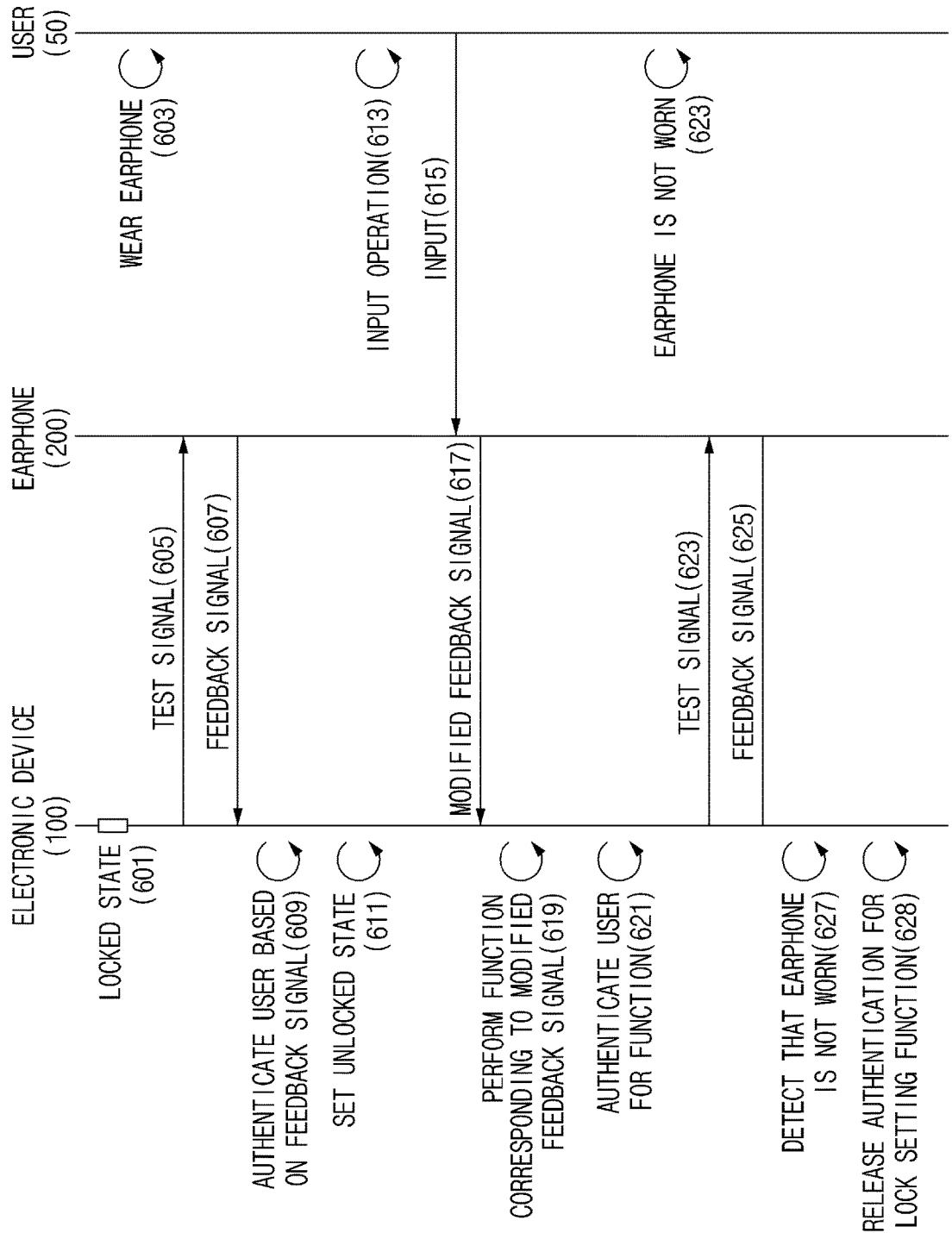
FIG. 6 is a diagram in which a user authentication method is performed, according to an embodiment.

FIG. 6 is a diagram of a user authentication method, according to an embodiment.

The electronic device (e.g., the electronic device 100 of FIG. 1B) may be referred to, for example, as a smartphone. The audio output device 200 may be referred to as the earphone 200 in which a separate microphone is not included but a speaker is used as a microphone. As an example, a scenario in which the user 50 wearing the earphone 200 executes a voice secretary program will be described. The voice secretary program may be referred to as a program for processing a control command inputted by utterance of the user 50.

At step 601, the electronic device 100 may be in a lock state. At step 603, the user 50 may connect the earphone 200 to the electronic device 100 and wear the earphone 200. At step 605, the electronic device 100 may transmit a test signal to the earphone 200 in the lock state. The electronic device 100 may transmit a test signal to the earphone 200 every specific period. At step 607, the electronic device 100 may receive a feedback signal from the earphone 200.

At step 609, the electronic device 100 may determine whether the user 50 is a previously registered user, based on the received feedback signal (user authentication operation). At step 611, when the user 50 is a previously registered user (authentication success), the electronic device 100 may be unlocked. The user 50 may use the electronic device 100 without any additional authentication actions (e.g., a password input, a fingerprint input, an utterance input for a security text, etc.). Through this authentication procedure, a program for providing an artificial intelligent service, such as a voice secretary program, may be provided intuitively and quickly.

At step 613, the user 50 may perform an input operation for executing a function of the earphone 200. The user 50 may perform two tap operations set to execute the voice secretary program. The input circuit of the earphone 200 may receive an input at step 615 and the electronic device 100 may receive a feedback signal modified by the input at step 617.

At step 619, the electronic device 100 may perform a function corresponding to the modified feedback. The electronic device 100 may execute the voice secretary program mapped to the feedback signal modified by the two tap operations.

At step 621, the electronic device 100 may perform user authentication for the function to be executed. The function may require user authentication for execution. The electronic device 100 may perform user authentication in response to the request. The electronic device 100 may perform authentication for the function based on the user authentication that has already been completed at step 609. Alternatively, the feedback signal may be transmitted from the earphone 200 again and the electronic device 100 may perform the authentication.

By executing the voice secretary program, the user authentication may be requested. When the authentication of the user 50 for the voice secretary program is completed, the user 50 may use the voice secretary program.

A program for which user authentication is required may include a first mode executed when there is no user authentication and a second mode executed when the user authentication is completed. In the first mode, some functions of the program may be restricted for security.

The voice secretary program may be first executed in the first mode (e.g., a normal mode). When the voice secretary program is executed in the first mode, some of the utterance commands of the user 50 may be restricted for security. When the user authentication is completed, the voice secretary program may be switched to the second mode (e.g., a master mode). The user 50 may use the electronic device 100 and other programs without limitations by wearing the earphone 200 without performing a separate operation for authentication (e.g., a password input, fingerprint authentication, a speech about a security phrase, etc.).

The electronic device 100 may detect the detachment of the earphone 200. The electronic device 100 may periodically transmit a test signal to the earphone 200 at step 623 and may receive a feedback signal corresponding to the test signal at step 625. At step 627, the electronic device 100 may detect from the feedback signal that the earphone 200 is not worn by the user 50. Alternatively, the electronic device 100 may be notified from the earphone 200 that the user has not worn the earphone. At step 628, when the electronic device 100 detects that the earphone 200 is not worn by the authenticated user 50, the electronic device 100 may release authentication for the function and lock the electronic device 100.

The voice secretary program may be terminated or switched from the second mode to the first mode again.

Figure 7:
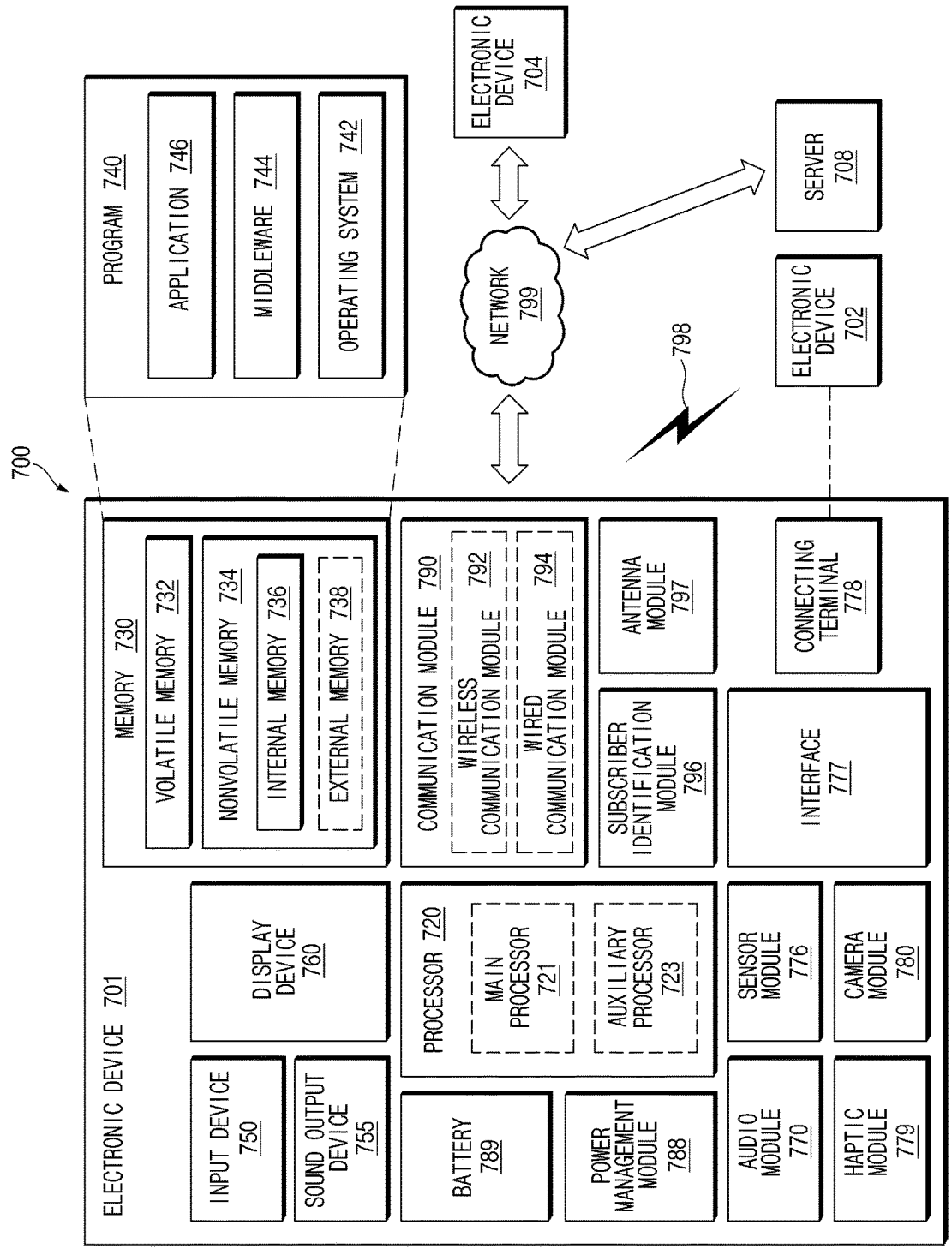
FIG. 7 is a block diagram of an electronic device in a network environment according to an embodiment.

FIG. 7 is a block diagram of an electronic device in a network environment according to an embodiment.

Referring to FIG. 7, an electronic device 701 may communicate with an electronic device 702 through a first network 798 (e.g., a short-range wireless communication) or may communicate with an electronic device 704 or a server 708 through a second network 799 (e.g., a long-distance wireless communication) in a network environment 700. According to an embodiment, the electronic device 701 may communicate with the electronic device 704 through the server 708. The electronic device 1001 may include a processor 720, a memory 730, an input device 750, a sound output device 755, a display device 760, an audio module 770, a sensor module 776, an interface 777, a haptic module 779, a camera module 780, a power management module 788, a battery 789, a communication module 790, a subscriber identification module 796, and an antenna module 797. At least one (e.g., the display device 760 or the camera module 780) among components of the electronic device 701 may be omitted or other components may be added to the electronic device 701. Some components may be integrated and implemented as in the case of the sensor module 1076 (e.g., a fingerprint sensor, an iris sensor, or an illuminance sensor) embedded in the display device 760 (e.g., a display).

The processor 720 may operate, for example, software (e.g., a program 740) to control at least one of other components (e.g., a hardware or software component) of the electronic device 701 connected to the processor 720 and may process and compute a variety of data. The processor 720 may load a command set or data, which is received from other components (e.g., the sensor module 776 or the communication module 790), into a volatile memory 732, may process the loaded command or data, and may store result data into a nonvolatile memory 734. According to an embodiment, the processor 720 may include a main processor 721 (e.g., a central processing unit (CPU) or an AP) and an auxiliary processor 723 (e.g., a graphic processing device, an image signal processor, a sensor hub processor, or a communication processor (CP)), which operates independently from the main processor 721, additionally or alternatively uses less power than the main processor 721, or is specified to a designated function. In this case, the auxiliary processor 723 may operate separately from the main processor 721 or embedded.

The auxiliary processor 723 may control, for example, at least some of functions or states associated with at least one component (e.g., the display device 760, the sensor module 776, or the communication module 790) among the components of the electronic device 701 instead of the main processor 721 while the main processor 721 is in an inactive (e.g., sleep) state or together with the main processor 721 while the main processor 721 is in an active (e.g., an application execution) state. According to an embodiment, the auxiliary processor 723 (e.g., the image signal processor or the CP) may be implemented as a part of another component (e.g., the camera module 780 or the communication module 790) that is functionally related to the auxiliary processor 723. The memory 730 may store a variety of data used by at least one component (e.g., the processor 720 or the sensor module 776) of the electronic device 701, for example, software (e.g., the program 740) and input data or output data with respect to commands associated with the software. The memory 730 may include the volatile memory 732 or the nonvolatile memory 734.

The program 740 may be stored in the memory 730 as software and may include, for example, an operating system 742, a middleware 744, or an application 746.

The input device 750 may be a device for receiving a command or data, which is used for a component (e.g., the processor 720) of the electronic device 701, from an outside (e.g., a user) of the electronic device 701 and may include, for example, a microphone, a mouse, or a keyboard.

The sound output device 755 may be a device for outputting a sound signal to the outside of the electronic device 701 and may include, for example, a speaker used for general purposes, such as multimedia play or recordings play, and a receiver used only for receiving calls. According to an embodiment, the receiver and the speaker may be either integrally or separately implemented.

The display device 760 may be a device for visually presenting information to the user of the electronic device 701 and may include, for example, a display, a hologram device, or a projector and a control circuit for controlling a corresponding device. According to an embodiment, the display device 760 may include a touch circuitry or a pressure sensor for measuring an intensity of pressure on the touch.

The audio module 770 may convert a sound and an electrical signal in dual directions. According to an embodiment, the audio module 770 may obtain the sound through the input device 750 or may output the sound through an external electronic device (e.g., the electronic device 702 (e.g., a speaker or a headphone)) wired or wirelessly connected to the sound output device 755 or the electronic device 701.

The sensor module 776 may generate an electrical signal or a data value corresponding to an operating state (e.g., power or temperature) inside or an environmental state outside the electronic device 701. The sensor module 776 may include, for example, a gesture sensor, a gyro sensor, a barometric pressure sensor, a magnetic sensor, an acceleration sensor, a grip sensor, a proximity sensor, a color sensor, an infrared sensor, a biometric sensor, a temperature sensor, a humidity sensor, or an illuminance sensor.

The interface 777 may support a designated protocol wired or wirelessly connected to the external electronic device 702. According to an embodiment, the interface 777 may include, for example, an HDMI (high-definition multimedia interface), a USB (universal serial bus) interface, an SD card interface, or an audio interface.

A connecting terminal 778 may include a connector that physically connects the electronic device 701 to the external electronic device 702, for example, an HDMI connector, a USB connector, an SD card connector, or an audio connector (e.g., a headphone connector).

The haptic module 779 may convert an electrical signal to a mechanical stimulation (e.g., vibration or movement) or an electrical stimulation perceived by the user through tactile or kinesthetic sensations. The haptic module 779 may include, for example, a motor, a piezoelectric element, or an electric stimulator.

The camera module 780 may shoot a still image or a video image. According to an embodiment, the camera module 780 may include, for example, at least one lens, an image sensor, an image signal processor, or a flash.

The power management module 788 may be a module for managing power supplied to the electronic device 701 and may serve as at least a part of a power management integrated circuit (PMIC).

The battery 789 may be a device for supplying power to at least one component of the electronic device 701 and may include, for example, a non-rechargeable (primary) battery, a rechargeable (secondary) battery, or a fuel cell.

The communication module 790 may establish a wired or wireless communication channel between the electronic device 701 and the external electronic device (e.g., the electronic device 702, the electronic device 704, or the server 708) and support communication execution through the established communication channel. The communication module 790 may include at least one communication processor operating independently from the processor 720 (e.g., the AP) and supporting the wired communication or the wireless communication. According to an embodiment, the communication module 790 may include a wireless communication module 792 (e.g., a cellular communication module, a short-range wireless communication module, or a GNSS (global navigation satellite system) communication module) or a wired communication module 794 (e.g., an LAN (local area network) communication module or a power line communication module) and may communicate with the external electronic device using a corresponding communication module among them through the first network 798 (e.g., the short-range communication network such as a Bluetooth, a WiFi direct, or an IrDA (Infrared Data Association)) or the second network 799 (e.g., the long-distance wireless communication network such as a cellular network, an internet, or a computer network (e.g., LAN or WAN)). The above-mentioned various communication modules 790 may be implemented into one chip or into separate chips, respectively.

According to an embodiment, the wireless communication module 792 may identify and authenticate the electronic device 701 using user information stored in the subscriber identification module 796 in the communication network.

The antenna module 797 may include one or more antennas to transmit or receive the signal or power to or from an external source. According to an embodiment, the communication module 790 (e.g., the wireless communication module 792) may transmit or receive the signal to or from the external electronic device through the antenna suitable for the communication method.

Some components among the components may be connected to each other through a communication method (e.g., a bus, a GPIO (general purpose input/output), an SPI (serial peripheral interface), or an MIPI (mobile industry processor interface)) used between peripheral devices to exchange signals (e.g., a command or data) with each other.

According to an embodiment, the command or data may be transmitted or received between the electronic device 701 and the external electronic device 704 through the server 708 connected to the second network 799. Each of the electronic devices 702 and 704 may be the same or different types as or from the electronic device 701. All or some of the operations performed by the electronic device 701 may be performed by another electronic device or a plurality of external electronic devices. When the electronic device 701 performs some functions or services automatically or by request, the electronic device 701 may request the external electronic device to perform at least some of the functions related to the functions or services, in addition to or instead of performing the functions or services by itself. The external electronic device receiving the request may carry out the requested function or the additional function and transmit the result to the electronic device 701. The electronic device 701 may provide the requested functions or services based on the received result as is or after additionally processing the received result. To this end, for example, a cloud computing, distributed computing, or client-server computing technology may be used.

Figure 8:
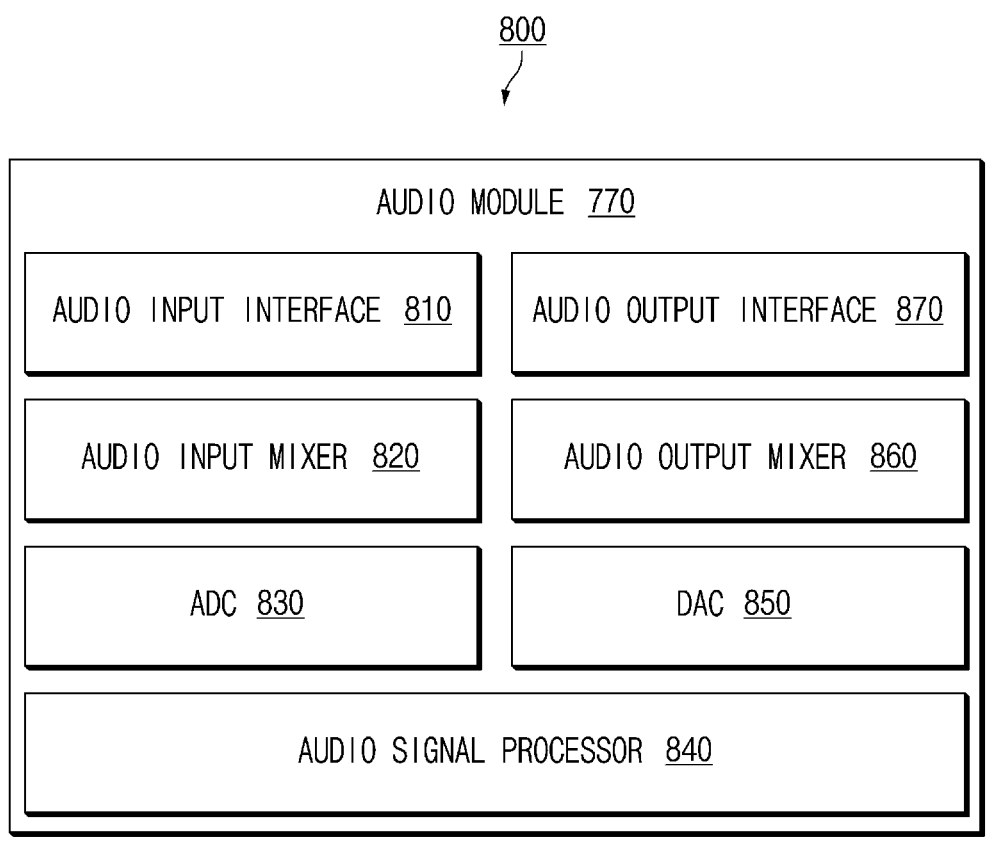
FIG. 8 is a block diagram 800 illustrating the audio module 770 according to an embodiment.

FIG. 8 is a block diagram 800 illustrating the audio module 770 according to an embodiment. Referring to FIG. 8, the audio module 770 may include, for example, an audio input interface 810, an audio input mixer 820, an analog-to-digital converter (ADC) 830, an audio signal processor

840, a digital-to-analog converter (DAC) 850, an audio output mixer 860, or an audio output interface 870.

The audio input interface 810 may receive an audio signal corresponding to a sound obtained from the outside of the electronic device 701 via a microphone (e.g., a dynamic microphone, a condenser microphone, or a piezo microphone) that is configured as part of the input device 750 or separately from the electronic device 701. For example, if an audio signal is obtained from the external electronic device 702 (e.g., a headset or a microphone), the audio input interface 810 may be connected with the external electronic device 702 directly via the connecting terminal 778, or wirelessly (e.g., Bluetooth™ communication) via the wireless communication module 792 to receive the audio signal. According to an embodiment, the audio input interface 810 may receive a control signal (e.g., a volume adjustment signal received via an input button) related to the audio signal obtained from the external electronic device 702. The audio input interface 810 may include a plurality of audio input channels and may receive a different audio signal via a corresponding one of the plurality of audio input channels, respectively. Additionally or alternatively, the audio input interface 810 may receive an audio signal from another component (e.g., the processor 720 or the memory 730) of the electronic device 701.

The audio input mixer 820 may synthesize a plurality of inputted audio signals into at least one audio signal. For example, according to an embodiment, the audio input mixer 820 may synthesize a plurality of analog audio signals inputted via the audio input interface 810 into at least one analog audio signal.

The ADC 830 may convert an analog audio signal into a digital audio signal. For example, according to an embodiment, the ADC 830 may convert an analog audio signal received via the audio input interface 810 or, additionally or alternatively, an analog audio signal synthesized via the audio input mixer 820 into a digital audio signal.

The audio signal processor 840 may perform various processing on a digital audio signal received via the ADC 830 or a digital audio signal received from another component of the electronic device 701. For example, the audio signal processor 840 may perform changing a sampling rate, applying one or more filters, interpolation processing, amplifying or attenuating a whole or partial frequency bandwidth, noise processing (e.g., attenuating noise or echoes), changing channels (e.g., switching between mono and stereo), mixing, or extracting a specified signal for one or more digital audio signals. According to an embodiment, one or more functions of the audio signal processor 840 may be implemented in the form of an equalizer.

The DAC 850 may convert a digital audio signal into an analog audio signal. For example, according to an embodiment, the DAC 850 may convert a digital audio signal processed by the audio signal processor 840 or a digital audio signal obtained from another component (e.g., the processor (720) or the memory (730)) of the electronic device 701 into an analog audio signal.

The audio output mixer 860 may synthesize a plurality of audio signals, which are to be outputted, into at least one audio signal. For example, according to an embodiment, the audio output mixer 860 may synthesize an analog audio signal converted by the DAC 850 and another analog audio signal (e.g., an analog audio signal received via the audio input interface 810) into at least one analog audio signal.

The audio output interface 870 may output an analog audio signal converted by the DAC 850 or, additionally or alternatively, an analog audio signal synthesized by the audio output mixer 860 to the outside of the electronic device 701 via the sound output device 755. The sound output device 755 may include, for example, a speaker, such as a dynamic driver or a balanced armature driver, or a receiver. According to an embodiment, the sound output device 755 may include a plurality of speakers. In such a case, the audio output interface 870 may output audio signals having a plurality of different channels (e.g., stereo channels or 5.1 channels) via at least some of the plurality of speakers. According to an embodiment, the audio output interface 870 may be connected with the external electronic device 702 (e.g., an external speaker or a headset) directly via the connecting terminal 778 or wirelessly via the wireless communication module 792 to output an audio signal.

The audio module 770 may generate, without separately including the audio input mixer 820 or the audio output mixer 860, at least one digital audio signal by synthesizing a plurality of digital audio signals using at least one function of the audio signal processor 840.

The audio module 770 may include an audio amplifier (e.g., a speaker amplifying circuit) that is capable of amplifying an analog audio signal inputted via the audio input interface 810 or an audio signal that is to be outputted via the audio output interface 870. The audio amplifier may be configured as a module separate from the audio module 770.

The electronic device according to various embodiments disclosed in the present disclosure may be various types of devices. The electronic device may include, for example, at least one of a portable communication device (e.g., a smartphone), a computer device, a portable multimedia device, a mobile medical appliance, a camera, a wearable device, or a home appliance. The electronic device according to an embodiment of the present disclosure should not be limited to the above-mentioned devices.

It should be understood that various embodiments of the present disclosure and terms used in the embodiments do not intend to limit technologies disclosed in the present disclosure to the particular forms disclosed herein; rather, the present disclosure should be construed to cover various modifications, equivalents, and/or alternatives of embodiments of the present disclosure. With regard to description of drawings, similar components may be assigned with similar reference numerals. As used herein, singular forms may include plural forms as well unless the context clearly indicates otherwise.

The term "module" used herein may represent, for example, a unit including one or more combinations of hardware, software and firmware. The term "module" may be interchangeably used with the terms "logic", "logical block", "part" and "circuit". The "module" may be a minimum unit of an integrated part or may be a part thereof. The "module" may be a minimum unit for performing one or more functions or a part thereof. For example, the "module" may include an application-specific integrated circuit (ASIC).

Various embodiments of the present disclosure may be implemented by software including an instruction stored in a machine-readable storage media readable by a machine (e.g., a computer). The machine may be a device that calls the instruction from the machine-readable storage media and operates depending on the called instruction and may include the electronic device. When the instruction is executed by the processor, the processor may perform a function corresponding to the instruction directly or using other components under the control of the processor. The instruction may include a code generated or executed by a compiler or an interpreter. The machine-readable storage media may be provided in the form of non-transitory storage media. Here, the term "non-transitory", as used herein, is a limitation of the medium itself (i.e., tangible, not a signal) as opposed to a limitation on data storage persistency.

The method according to various embodiments disclosed in the present disclosure may be provided as a part of a computer program product. The computer program product may be traded between a seller and a buyer as a product. The computer program product may be distributed in the form of machine-readable storage medium (e.g., a compact disc read only memory (CD-ROM)) or may be distributed only through an application store (e.g., a Play Store™). In the case of online distribution, at least a portion of the computer program product may be temporarily stored or generated in a storage medium such as a memory of a manufacturer's server, an application store's server, or a relay server.

Each component (e.g., the module or the program) according to various embodiments may include at least one of the above components, and a portion of the above sub-components may be omitted, or additional other sub-components may be further included. Alternatively or additionally, some components (e.g., the module or the program) may be integrated in one component and may perform the same or similar functions performed by each corresponding components prior to the integration. Operations performed by a module, a programming, or other components according to various embodiments of the present disclosure may be executed sequentially, in parallel, repeatedly, or in a heuristic method. Also, at least some operations may be executed in different sequences, omitted, or other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
    an interface;
    a memory configured to store user authentication information that includes authentication data and user authority information, wherein the authentication data are related to feedback signals corresponding to registered users of the electronic device and the user authority information includes a list of programs that are authenticated by an external device; and
    a processor configured to:
    transmit a test signal to the external device for a time shorter than a specified time;
    receive a feedback signal corresponding to the test signal;
    set an audio signal output level based on the received feedback signal;
    receive an input of a user;
    output an audio signal at the set output level by using the external device connected to the electronic device through the interface, in response to the input of the user;
    obtain an audio signal reflected on a part of the user of the outputted audio signal, by using the external device;
    identify the user as an authenticated user among the registered users by using the reflected audio signal; and
    execute a specified function in an unlocked state of the electronic device when the user is authenticated for the electronic device based on the user authentication information,
    wherein, when an authentication for the user is completed, execute programs in the list without any additional authentication.

2. The electronic device of claim 1, wherein the processor is further configured to:
    obtain a voice input corresponding to the specified function from the user; and
    transmit the voice input or text data corresponding to the voice input to another external electronic device to allow the another external electronic device to generate an instruction related to the specified function by using the voice input or the text data, and
    execute the specified function based on the instruction.

3. The electronic device of claim 1, wherein the external device includes an earphone.

4. An electronic device comprising:
    an interface configured to connect an audio output device and the electronic device;
    an analog/digital (A/D) converter;
    an audio circuit configured to transmit an audio signal to the audio output device connected to the electronic device through the interface;
    a memory including a file having restricted user access, user authentication information about a registered user of the electronic device, and instructions; and
    at least one processor electrically connected to the memory,
    wherein, when executed, the instructions cause the at least one processor to:
    transmit a test signal to the audio output device, through the audio circuit, for a first time shorter than a specified time;
    receive a feedback signal corresponding to the test signal from the audio output device through the audio circuit;
    unlock the electronic device in a lock state when a user wearing the audio output device is indicated as the registered user based on the received feedback signal and the user authentication information; and
    when the user wearing the audio output device is indicated as the registered user based on the received feedback signal and the user authentication information, permit access to the file without additional authentication,
    wherein an output level of the audio signal is set based on an impedance of the audio output device determined by the A/D converter and the received feedback signal.

5. The electronic device of claim 4, wherein the audio circuit includes an analog/digital (A/D) converter, and
    wherein, when executed, the instructions further cause the at least one processor to:
    obtain pulse code modulation (PCM) data corresponding to the received feedback signal through the A/D converter; and
    compare the PCM data with the user authentication information.

6. The electronic device of claim 4, wherein the feedback signal corresponding to the test signal transmitted is received for the specified time.

7. The electronic device of claim 4, wherein, when executed, the instructions further cause the at least one processor to:
    transmit the test signal to the audio output device every specified period.

8. The electronic device of claim 4, wherein, when executed, the instructions further cause the at least one processor to:

lock the electronic device in an unlocked state when a state where the audio output device is not worn by the authenticated user is detected.

9. The electronic device of claim 4, wherein, when executed, the instructions further cause the at least one processor to:
when a program requiring authentication of the user is executed and the user wearing the audio output device is indicated as the registered user based on the received feedback signal and the user authentication information, change an unauthenticated state of the program to an authenticated state.

10. The electronic device of claim 9, wherein, when executed, the instructions further cause the at least one processor to:
when a state where the authenticated user does not wear the audio output device is detected, lock the electronic device in the unlocked state and change the authenticated state of the program to an unauthenticated state.

11. The electronic device of claim 4, wherein, when executed, the instructions further cause the at least one processor to:
receive the feedback signal modified in accordance with an input obtained through an input circuit included in the audio output device; and
execute at least one function corresponding to the modified feedback signal.

12. The electronic device of claim 11, wherein, when executed, the instructions further cause the at least one processor to:
receive the modified feedback signal in accordance with one of a touch input and a tap input through the input circuit.

13. The electronic device of claim 11, wherein the input circuit is arranged on the interface.

14. A method performed by an electronic device, the method comprising:
transmitting a test signal to an audio output device connected to the electronic device for a previously specified time,
receiving a feedback signal corresponding to the test signal from the audio output device;
when a user wearing the audio output device is indicated as a registered user of the electronic device, based on the received feedback signal and user authentication information, unlocking the electronic device;
transmit the test signal to the audio output device for a time shorter than the previously specified time;
determine an impedance of the audio output device through another feedback signal corresponding to the test signal transmitted for the time shorter than the previously specified time; and
set an output level of the audio signal based on the determined impedance of the audio output device determined by an analog/digital (A/D) converter of the audio output device.

15. The method of claim 14, further comprising:
obtaining pulse code modulation (PCM) data corresponding to the received feedback signal and comparing the PCM data with the user authentication information.

16. The method of claim 15, further comprising:
when a state where an authenticated user does not wear the audio output device is detected, locking the electronic device.

17. The method of claim 14, further comprising:
when a program requiring authentication of the user is executed and the user wearing the audio output device is indicated as the registered user based on the received feedback signal and the user authentication information, changing an unauthenticated state of the program to an authenticated state.

18. The method of claim 17, further comprising:
when a state where the authenticated user does not wear the audio output device is detected, locking the electronic device and changing the authenticated state of the program to an unauthenticated state.

* * * * *